United States Patent [19]

Barton et al.

[11] Patent Number: 5,030,269
[45] Date of Patent: Jul. 9, 1991

[54] NOVEL ANTIDOTED HERBICIDAL COMPOSITION

[75] Inventors: John E. D. Barton, Reading; John W. Slater, Twyford; David J. Collins, Crowthorne; Bogdan Kowalczyk, Maidenhead, all of United Kingdom

[73] Assignee: Imperial Chemical Industries PLC, London, England

[21] Appl. No.: 151,282

[22] Filed: Feb. 1, 1988

[30] Foreign Application Priority Data

Feb. 5, 1987 [GB] United Kingdom ............ 8702613

[51] Int. Cl.$^5$ .................... A01N 43/42; A01N 31/16; A01N 41/10; A01N 37/34
[52] U.S. Cl. ............................. 71/88; 71/98; 71/103; 71/105; 71/109; 71/116; 71/117; 71/118; 71/121
[58] Field of Search ............... 71/88, 98, 103, 116, 71/117, 118, 94, 109, 105, 121

[56] References Cited

U.S. PATENT DOCUMENTS

| 4,414,020 | 11/1983 | Heier et al. | 71/108 |
| 4,666,510 | 5/1987 | Watson et al. | 71/103 |
| 4,668,276 | 5/1987 | Handte et al. | 71/88 |
| 4,717,418 | 6/1988 | Warner et al. | 71/98 |

Primary Examiner—Glennon H. Hollrah
Assistant Examiner—Brian G. Bembenick
Attorney, Agent, or Firm—Cushman, Darby & Cushman

[57] ABSTRACT

The present invention relates to a process for protecting crop plants against phytotoxic side effects of compounds of formula:

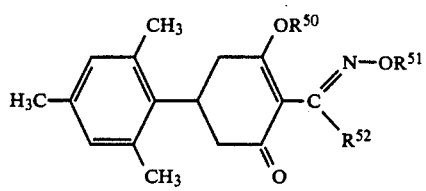

and

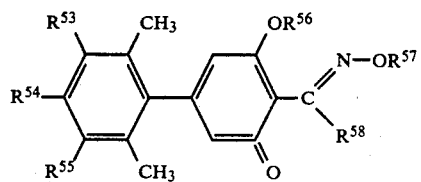

which comprises treating the plants, parts of plants or fertile soils for plants with compounds of the formula:

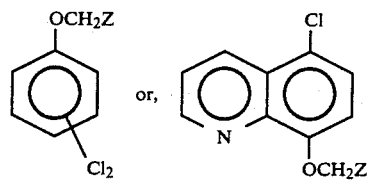

before, after or at the same time.

4 Claims, No Drawings

NOVEL ANTIDOTED HERBICIDAL COMPOSITION

This invention relates to herbicidal compositions and to their use in agriculture.

German Offenlegungsschrift No. 34 04 401 A1 discloses compounds of formula (I)

$$Ar-O-A-Z \qquad (I)$$

wherein

Ar is a phenyl, naphthyl or quinolyl optionally substituted by from one to three halogen atoms, and/or one or two groups selected from trifluoromethyl, $C_{1-4}$ alkyl, $C_{1-4}$ alkoxy, nitrile or nitro; A is a $C_{1-4}$ linear or branched optionally unsaturated hydrocarbon chain; and Z is a moiety of formula:

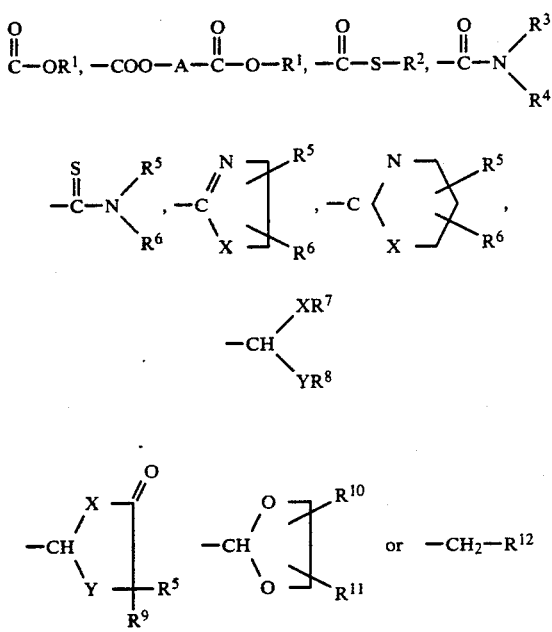

wherein $R^1$ is hydrogen, $C_{1-12}$ alkyl optionally substituted with 1 to 3 groups selected from fluorine, chlorine, bromine and/or 1 to 2 groups selected from CN, OH, $C_{1-6}$ alkoxy, $C_{1-4}$ alkylthio, $C_{1-4}$ alkylsulphinyl, $C_{1-4}$ alkylsulphonyl, $C_{1-6}$ alkoxy-$C_{2-6}$ alkoxy, halogenoalkoxy, methoxyethoxyethoxy, $C_{1-4}$ alkylamino, di($C_{1-4}$)alkylamino, $C_{1-4}$ alkylcarbonyl, a saturated or unsaturated heterocyclic ring containing from 2 to 7 atoms from 1 to 3 of which are selected from sulphur, oxygen or nitrogen, said ring being optionally benzofused and/or substituted by halogen and/or $C_{1-4}$ alkyl; or a phenyl, benzyl, phenoxy or benzyloxy group of optionally substituted by one or two groups selected from fluorine, chlorine bromine and/or $C_{1-4}$ alkyl; $C_{5-6}$ cycloalkyl optionally substituted by halogen or methyl; $C_{3-6}$ alkenyl, halo-($C_{3-6}$) alkenyl or $C_{5-6}$ cycloalkenyl; $C_{3-4}$ alkynyl optionally substituted by one or two $C_{1-6}$ alkyl, phenyl, halogen or $C_{1-2}$ alkoxy groups; phenyl optionally substituted by from the two of three groups selected from $C_{1-4}$ alkyl, $C_{1-4}$ alkoxy, halogen, $NO_2$ or trifluoromethyl;

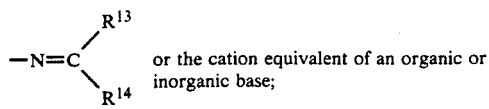

or the cation equivalent of an organic or inorganic base;

$R^2$ is $C_{1-6}$ alkyl, phenyl ($C_{1-2}$) alkyl wherein the phenyl portion is optionally substituted by one or two groups selected from $C_{1-4}$ alkyl and/or halogen; $C_{3-6}$ alkenyl; phenyl optionally substituted by one or two groups selected from $C_{1-4}$ alkyl or halogen; or $C_{1-4}$ alkoxycarbonyl $C_{1-3}$ alkyl;

$R^3$ is hydrogen, $C_{1-6}$ alkyl, $C_{1-4}$ alkoxy, hydroxy $C_{1-4}$ alkyl, $C_{5-6}$ cycloalkyl, $C_{3-6}$ alkynyl or a group $-NR^5R^6$;

$R^4$ is hydrogen, $C_{1-6}$ alkyl hydroxy $C_{1-4}$ alkyl, cyclopropyl, $C_{3-6}$ alkenyl; or phenyl optionally substituted by from one to three groups selected from $C_{1-4}$ alkyl, $C_{1-4}$ alkoxy, halogen or trifluoromethyl; or $R^3$ and $R^4$ together form an alkylene bridge of 2,4 or 5 carbon atoms, in which one $-CH_2$ group is optionally replaced by and O, NH or $NC_{(1-4)}$alkyl group;

$R^5$ and $R^6$ are independently selected from hydrogen or $C_{1-4}$ alkyl;

X and Y are independently selected from O, S, NH or $N(C_{1-4})$alkyl;

$R^7$ and $R^8$ are independently selected from $C_{1-6}$ alkyl optionally substituted by one or two hydrogen, $C_{1-4}$ alkoxy, phenyl or benzyl groups;

$R^9$ is hydrogen, $C_{1-6}$ alkyl or phenyl;

$R^{10}$ and $R^{11}$ are independently selected from hydrogen or $C_{1-6}$ alkyl optionally substituted by halogen, hydroxy or $C_{1-6}$ alkoxy;

$R^{13}$ is hydrogen or $C_{1-6}$ alkyl;

$R^{14}$ is hydrogen, $C_{1-6}$ alkyl, $C_{2-6}$ alkynyl or phenyl with the proviso that $R^{13}$ and $R^{14}$ are not both hydrogen; and

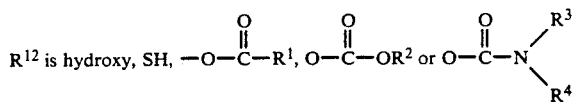

The compounds are said to reduce crop damage caused by the use of certain herbicides.

Further compounds having this effect are compounds of formula (II) as described in EP-A-31938.

$$Ar'-X'-C_pH_{2p}-R^{15} \qquad (II)$$

wherein Ar' is phenyl optionally substituted by one or two groups selected from chlorine or bromine and/or one group selected from $CF_3$, $C_{1-4}$ alkyl, $C_{1-4}$ alkoxy, CN, $NO_2$, phenyl, benzyl or para-phenoxy, wherein the benzyl or phenoxy groups may themselves be substituted on the phenyl ring by up to 2 groups selected from chlorine, bromine, CN, $NO_2$ or $CF_3$; or naphthyl optionally substituted by one or two groups selected from chlorine, bromine, $C_{1-4}$ alkyl, CN, $NO_2$ or $CF_3$;

X' is oxygen, sulphur, SO or $SO_2$;

p is 1, 2 or 3;

$R^{15}$ is CN or $C(NH_2)NOR^{16}$ wherein $R^{16}$ is hydrogen, $C_{1-4}$ alkyl optionally substituted by chlorine, bromine, CN, $NO_2$, $-COOC_{1-4}$ alkyl or $CONR^{17}R^{18}$; $-COR^{19}$, $-SO_3R^{20}$ or

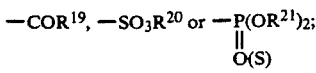

R$^{17}$ and R$^{18}$ or C$_{1-18}$ alkyl or R$^{17}$ and R$^{18}$ together with the nitrogen atom to which they are attached form a piperdine, pyrrolidine or morpholine ring;

R$^{19}$ is C$_{1-3}$ alkyl, phenyl or benzyl wherein the latter can be substituted in the phenyl ring by one or two groups selected from chlorine, bromine, CN, NO$_2$, CF$_3$ or C$_{1-3}$ alkyl;

R$^{20}$ is C$_{1-4}$ alkyl, phenyl or tolyl; and

R$^{21}$ is C$_{1-4}$ alkyl

Particular examples of compounds of formula (II) are described in EP-A-31938 and also in Canadian Patent No. 1202438.

EP-A-0174562 describes plant protecting means of formula (III)

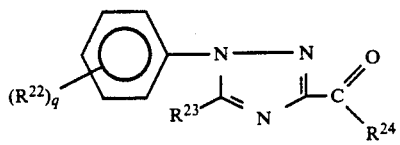

wherein R$^{22}$ are the same or different groups selected from halogen, nitro, cyano, trifluoromethyl, (C$_{1-4}$)alkyl, (C$_{1-4}$)alkoxy, (C$_{1-4}$)alkythio, wherein the alkyl, alkoxy and alkythio groups can be substituted by one or more halogen atoms, in particular fluorine or chlorine, (C$_{3-6}$)cycloalkyl optionally substituted by C$_{1-4}$alkyl or phenoxy optionally substituted by one or more halogen and/or a single trifluoromethyl group;

R$^{23}$ is hydrogen, (C$_{1-4}$)alkyl which can be completely or partially substituted by halogen atoms and/or by a single (C$_{1-4}$)alkoxy, (C$_{2-6}$)alkenyl, (C$_{2-6}$)alkynyl or C$_{3-6}$ cycloalkyl, which can be substituted by (C$_{1-4}$)alkyl and/or a dichlorovinyl moiety;

R$^{24}$ is hydroxy, (C$_{1-4}$)alkyl, (C$_{3-6}$)cycloalkoxy, phenyl (C$_{1-6}$)alkoxy, phenoxy, (C$_{2-6}$)alkenyloxy, (C$_{2-6}$)alkynyloxy, (C$_{1-6}$)alkoxy, (C$_{1-6}$)alkylthio wherein the alkoxy or alkylthio groups can be substituted by (C$_{1-2}$)alkoxy, mono- or di- (C$_{1-4}$)alkylaminocarbonyl, phenylaminocarbonyl, N-(C$_{1-4}$)alkylaminocarbonyl, phenylaminocarbonyl, N-(C$_{1-4}$)alkyl-phenylamino carbonyl, mono- or di- (C$_{1-6}$)alkyl amino, (C$_{1-6}$) alkyl-carbonyloxy, (C$_{1-2}$)alkylthio, cyano or halogen; or R$^{24}$ is a group of formula

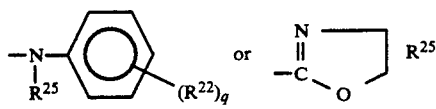

wherein R$^{25}$ is hydrogen or (C$_{1-4}$)alkyl; or R$^{24}$ is mono or di (C$_{1-4}$)alkylamino, (C$_{5-6}$) cycloalkylamino, piperdino, morpholino or 2,6-dimethylmorpholino, or a group of formula

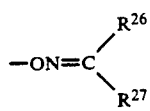

wherein R$^{26}$ and R$^{27}$ are the same or different (C$_{1-4}$) alkyl groups, or R$^{26}$ and R$^{27}$ together form a 5, 6 or 7 membered cycloalkyl ring; and q is 0, 1, 2 or 3 and;

where R$^{24}$ is OH, agriculturally acceptable salts thereof.

EP-A-0163-236 describes additional additives for reducing the phytotoxicity of plants having formula IV

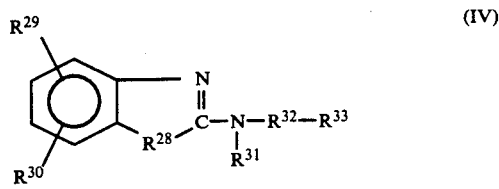

wherein R$^{28}$ is oxygen or sulphur;

R$^{29}$ and R$^{30}$ are hydrogen, halogen (C$_{1-4}$)alkyl, C$_{1-4}$alkoxy, CN, NO$_2$ or CF$_3$ R$^{31}$ is hydrogen or (C$_{1-4}$)alkyl;

R$^{32}$ is straight or branched chain (C$_{1-8}$)alkyl from which 1-3 carbon atoms are arranged between the amine group and the group R$^{33}$; methylthio C$_{1-3}$alkylene, phenyl (C$_{1-3}$)alkylene or phenylene

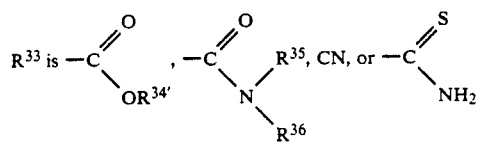

where R$^{34}$ is hydrogen, C$_{1-8}$ alkyl optionally substituted with halogen or C$_{1-2}$ alkoxy, (C$_{3-4}$)alkenyl, (C$_{3-4}$)alkynyl or the cation of an inorganic or organic base;

R$^{35}$ is hydrogen or (C$_{1-6}$)alkyl;

R$^{36}$ is hydrogen, C$_{1-6}$ alkyl or phenyl optionally substituted by one or two halogen, (C$_{1-4}$)alkyl or C$_{1-4}$alkoxy groups; or R$^{35}$ and R$^{36}$ together with the nitrogen atom to which they are attached form a pyrrolidino, piperdino or morpholino ring.

The applicants have found that the above described compounds of formula (I), (II), (III) and (IV) show a safening effect when employed in combination with certain other herbicides.

As used herein the expression "safening effect" means that the compounds antagonise the activity of the herbicide against one or more crops, and show little or no antagonism on one or more weeds.

Herbicidally active cyclohexanediones include compounds of formula (V)

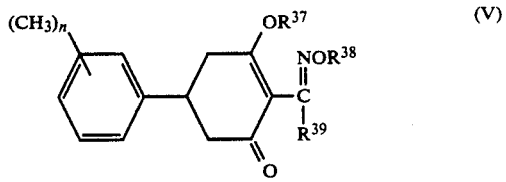

where

R$^{37}$ is selected from the group consisting of: hydrogen; C$_1$ to C$_6$ alkyl; C$_2$ to C$_6$ alkenyl; C$_2$ to C$_6$ alkynyl; substituted C$_1$ to C$_6$ alkyl wherein the alkyl group is substituted with a substituent selected from the group consisting of C$_1$ to C$_6$ alkoxy, C$_1$ to C$_6$ alkylthio, (C$_1$ to $C_6$ alkoxy) carbonyl, phenyl and substituted phenyl wherein the benzene ring is substituted with from one to three substituents selected from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio; $C_1$ to $C_6$ (alkyl) sulfonyl; benzene sulfonyl; substituted benzenesulfonyl wherein the benzene ring is substituted with from one to three substituents selected from the group consisting of halogen; nitro, cyano, $C_1$ to $C_6$ alkyl, $C_1$ to $C_6$ haloalkyl, $C_1$ to $C_6$ alkoxy and $C_1$ to $C_6$ alkylthio; an acyl group; and an inorganic or organic cation;

$R^{38}$ is selected from the group consisting of: $C_1$ to $C_6$ alkyl; $C_2$ to $C_6$ alkenyl; $C_2$ to $C_6$ haloalkenyl; $C_2$ to $C_6$ alkynyl; $C_2$ to $C_6$ haloalkynyl; substituted $C_1$ to $C_6$ alkyl wherein the alkyl group is substituted with a substituent selected from the group consisting of halogen, $C_1$ to $C_6$ alkoxy, $C_1$ to $C_6$ alkylthio, phenyl and substituted phenyl wherein the benzene ring is substituted with from one to three substituents selected from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio;

$R^{39}$ is selected from the group consisting of: $C_1$ to $C_6$ alkyl; $C_1$ to $C_6$ fluoroalkyl; $C_2$ to $C_6$ alkenyl; $C_2$ to $C_6$ alkynyl; and phenyl; and n is an integer chosen from 2 to 5.

These compounds and their preparation are described in Patent No. EP-A-0080301.

Further herbicidal cyclohexane diones and their preparation are described and claimed in EP-B-0085529. These compounds can be represented by formula (VI):

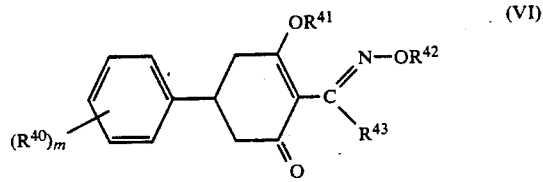

wherein $R^{40}$, which may be the same or different, are selected from the group consisting of: halogen; nitro; cyano; $C_1$ to $C_6$ alkyl; $C_1$ to $C_6$ alkyl substituted with a substituent selected from the group consisting of halogen, nitro, hydroxy, $C_1$ to $C_6$ alkoxy and $C_1$ to $C_6$ alkylthio; $C_2$ to $C_6$ alkenyl; $C_2$ to $C_6$ alkynyl; hydroxy; $C_1$ to $C_6$ alkoxy; $C_1$ to $C_6$ alkoxy substituted with a substituent selected from halogen and $C_1$ to $C_6$ alkoxy; $C_2$ to $C_6$ alkenyloxy; $C_2$ to $C_6$ alkynyloxy; $C_2$ to $C_6$ alkanoyloxy; ($C_1$ to $C_6$ alkoxy)carbonyl; $C_1$ to $C_6$ alkylthio; $C_1$ to $C_6$ alkylsulfinyl; $C_1$ to $C_6$ alkylsulfonyl; sulfamoyl; N-($C_1$ to $C_6$ alkyl)sulfamoyl; N,N-di($C_1$ to $C_6$ alkyl)sulfamoyl; benzyloxy, substituted benzyloxy wherein the benzene ring is substituted with from one to three substituents selected from the group consisting of halogen, nitro, $C_1$ to $C_6$ alkyl, $C_1$ to $C_6$ alkoxy and $C_1$ to $C_6$ haloalkyl; the group $NR^{44}R^{45}$ wherein $R^{44}$ and $R^{45}$ are independently selected from the group consisting of hydrogen, $C_1$ to $C_6$ alkyl, $C_2$ to $C_6$ alkanoyl, benzoyl and benzyl; the groups formyl and $C_2$ to $C_6$ alkanoyl and the oxime, imine and Schiff base derivatives thereof; and at least one of X is not selected from the group consisting of halogen, $C_1$ to $C_6$ alkyl and $C_1$ to $C_6$ alkoxy;

$R^{41}$ is selected from the group consisting of: hydrogen; $C_1$ to $C_6$ alkyl; $C_2$ to $C_6$ alkenyl; $C_2$ to $C_6$ alkynyl; substituted $C_1$ to $C_6$ alkyl wherein the alkyl group is substituted with a substituent selected from the group consisting of $C_1$ to $C_6$ alkoxy, $C_1$ to $C_6$ alkylthio, phenyl and substituted phenyl wherein the benzene ring is substituted with from one to three substituents selected from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio; $C_1$ to $C_6$ (alkyl) sulfonyl; benzenesulfonyl; substituted benzenesulfonyl wherein the benzene ring is substituted with from one to three substituents selected from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio; and acyl group; and an inorganic cation;

$R^{42}$ is selected from the group consisting of $C_1$ to $C_6$ alkyl; $C_2$ to $C_6$ alkenyl; $C_2$ to $C_6$ haloalkenyl; $C_2$ to $C_6$ alkynyl; $C_2$ to $C_6$ haloalkynyl; substituted $C_1$ to $C_6$ alkyl wherein the alkyl group is substituted with a substituent selected from the group consisting of halogen, $C_1$ to $C_6$ alkoxy, $C_1$ to $C_6$ alkythio, phenyl and substituted phenyl wherein the benzene ring is substituted with from one to three substituents selected from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio;

$R^{43}$ is selected from the group consisting of: $C_1$ to $C_6$ alkyl; $C_1$ to $C_6$ fluoroalkyl; $C_2$ to $C_6$ alkenyl; $C_2$ to $C_6$ alkynyl; and phenyl; and m is an integer chosen from 3 to 5.

According to the present invention there is provided a herbicidal composition comprising a compound of formula (V) or (VI) as hereinbefore defined in combination with a compound of formula (I), (II), (III) or (IV) as hereinbefore defined.

Many compounds of formula (I) and (II) are exemplified in DE-OS-3404401 and EP-A-0031938 respectively and these disclosures are incorporated herein by reference. Of the compounds of formula (I) a prefered sub-group for use in the present invention are compounds of formula (VII)

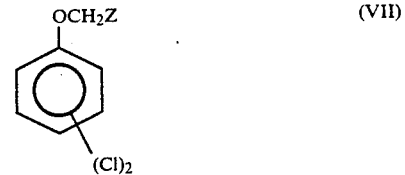

where Z is as hereinbefore defined.

Most suitable groups for use in a compound of formula (VII) are $-CO_2R^1$ wherein $R^1$ is as hereinbefore defined and is preferably hydrogen or $C_{1-6}$ alkyl, $-C(O)NR^3R^4$ wherein $R^3$ and $R^4$ are as hereinbefore defined and are preferably hydrogen or $C_{1-6}$ alkyl; or $-C(S)NR^5R^6$ wherein $R^5$ and $R^6$ are as hereinbefore defined, preferably hydrogen.

A preferred sub-group of compounds of formula (II) are those of formula (VIII)

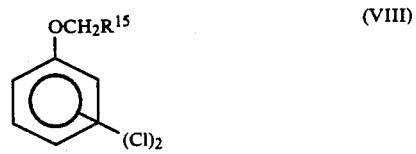

wherein $R^{15}$ is as hereinbefore defined.

Preferably $R^{15}$ is cyano.

Compounds of formula (VII) and (VIII) are particularly useful for reducing the toxicity of herbicides of formula (V) and (VI) towards temperature crops such as wheat and barley.

In particular in the compounds of formula (VII) and (VII) the two chlorine substituents are located at 3 and 4- or 3 and 5- positions on the phenyl ring.

A further preferred sub-group of compounds of formula (I) are compounds where Ar is quinolinyl in particular compounds of formula (IX):

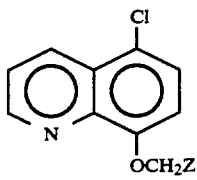
(IX)

wherein Z is as hereinbefore defined.

Preferably Z is selected from —C(O)OR$^1$ or —C(O)NR$^3$R$^4$ wherein R$^1$, R$^3$ and R$^4$ are as hereinbefore defined.

Most preferably R$^1$ is hydrogen or C$_{1-6}$ alkyl, and R$^3$ and R$^4$ are hydrogen.

For warm season crops such as maize, it is preferable that for a compound of formula (IX) where Z is —CO$_2$R$^1$, R$^1$ is not hydrogen or methyl.

Compounds of formula (III) are described and exemplified in EP-A-0174562 the text of which is incorporated herein by reference.

A preferred sub-group of the compounds of formula (III) are compounds of formula (X)

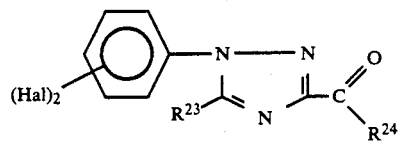
(X)

wherein Hal is halogen such as chlorine, and R$^{23}$ and R$^{24}$ are as hereinbefore defined.

Preferably the two halogen atoms on the phenyl ring are at the 2- and 4- positions.

Preferably R$^{23}$ is C$_{1-6}$alkyl such as methyl.

Preferably R$^{24}$ is OH or O(C$_{1-6}$alkyl) such as ethoxy.

Compounds of formula (X) are most effective in preventing phytotoxic effects of the above mentioned herbicides on crops such as maize.

Compounds of formula (IV) are exemplified in EP-A-0163236 which is incorporated herein by reference. A preferred sub-group of compounds of formula (IV) are compounds of formula (XI)

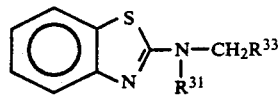
(XI)

wherein R$^{31}$ and R$^{33}$ are as hereinbefore defined.

Preferably R$^{31}$ is hydrogen and R$^{33}$ is —CO$_2$R$^{34}$ where R$^{34}$ is C$_{1-8}$ alkyl such as ethyl.

Compounds of formula (XI) show the most useful safening effect when used in temperate crops such as wheat and barley.

Another preferred sub-group of compounds of formula (IV) are compounds of formula (XII)

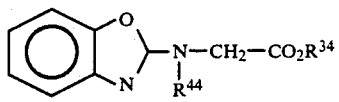
(XII)

wherein R$^{44}$ is C$_{1-4}$ alkyl such as methyl and R$^{34}$ is as hereinbefore defined, in particular C$_{1-8}$ alkyl such as ethyl.

Compounds of formula (XII) show the most useful safening effect in relation to warm season crops such as maize.

The herbicides for use in the invention are those described in EP-A-0080301 and EP-B-0085529, the subject matter of these specifications are incorporated herein by reference.

A preferred sub-group of the compounds of formula (V) are those where R$^{37}$ is selected from the group consisting of: hydrogen; C$_2$ to C$_6$ alkanoyl; benzoyl and substituted benzoyl wherein the benzene ring is substituted with from 1 to 3 substituents selected from the group consisting of halogen, nitro, C$_1$ to C$_6$ alkyl and C$_1$ to C$_6$ alkyl and C$_1$ to C$_6$ alkoxy; and an inorganic or organic cation selected from the alkali metal ions, the alkaline earth metal ions, transition metal ions and the ammonium ion R$^{46}$, R$^{47}$, R$^{48}$, R$^{49}$ N$^+$ wherein R$^{46}$, R$^{47}$, R$^{48}$ and R$^{49}$ are independently selected from the group consisting of: hydrogen; C$_1$ to C$_{10}$ alkyl; and substituted C$_1$ to C$_{10}$ alkyl wherein the alkyl group is substituted with a substituent selected from the group consisting of hydroxy and C$_1$ to C$_6$ alkoxy;

R$^{38}$ is selected from the group consisting of: C$_1$ to C$_6$ alkyl; C$_2$ to C$_6$ alkenyl; C$_2$ to C$_6$ alkynyl; C$_1$ to C$_6$ haloalkyl; C$_2$ to C$_6$ haloalkenyl; C$_1$ to C$_6$ alkyl substituted with C$_1$ to C$_6$ alkoxy; C$_1$ to C$_6$ alkyl substituted with C$_1$ to C$_6$ alkylthio; and benzyl and substituted with from one to three substituents selected from the group consisting of halogen, nitro and C$_1$ to C$_6$ alkyl;

R$^{39}$ is selected from the group consisting of C$_1$ to C$_6$ alkyl; and n is integer chosen from 3 to 5.

Particularly preferred compounds of formula (V) are compounds of formula (XIII)

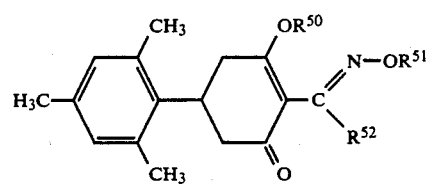
(XIII)

wherein:

R$^{50}$ is selected from hydrogen, sodium and potassium;

R$^{51}$ is selected from ethyl and allyl; and

R$^{52}$ is selected from ethyl and n-propyl.

A particularly preferred compound of formula (V) for use in the composition is the compound of formula XIV

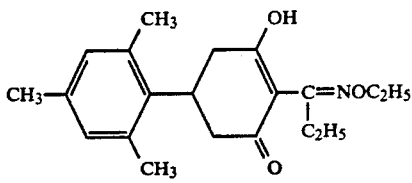

Turning now to the compounds of formula (VI), a preferred sub-group of compounds are compounds of formula (XIV):

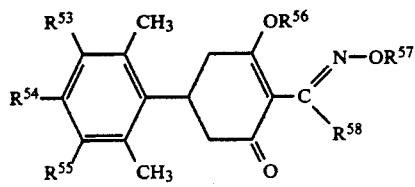

wherein
$R^{53}$ is selected from the group consisting of methylmercapto, nitromethyl, methoxymethyl, ethoxymethyl, methylsulfinyl, methylsulfonyl, acetyl, propionyl, butyryl sulfamoyl and N,N-di(methyl)sulfamoyl;
$R^{54}$ is selected from hydrogen and methyl;
$R^{55}$ is selected from hydrogen, methyl and ethyl;
$R^{56}$ is selected from hydrogen, sodium and potassium;
$R^{57}$ is selected from ethyl and allyl; and
$R^{58}$ is selected from ethyl and n-propyl.

The compounds of the general formulae (I) (II), (III) or (IV) is applied in low, i.e., subtoxic, concentrations in conjunction with a compound of formula (V) or (VI), and are then capable of reducing the harmful effects of the latter on the graminaceous crop, without impairing its herbicidal usefulness.

As a result of this the field of use of the herbicide can be increased considerably. The present invention also relates, therefore, to a process for protecting crop plants against phytotoxic side effects of compounds of formula (V) and (VI), which comprises treating the plants, parts of plants or fertile soils for plants with a compounds of the formula (I), (II), (III) or (IV) before, after or at the same time as (V) or (VI).

The composition, according to the invention, can be used as a selective agent for combating grass weeds in monocotyledonous crop plants, in particular species of cereals, such as maize, wheat, barley, rice and sorghum.

The selected herbicide ratio can vary within wide limits between 0.1 and 20 parts of compound of formula (I), (II), (III) or (IV) to 1 part of herbicide. The optimum ratio depends on the particular compound of formula (I), (II), (III) or (IV) and the compound of formula (V) or (VI) employed and on the nature of the crop plants to be treated.

This can be determined by routine methods by the skilled man.

Preferably the weight ratio additive: herbicide is (0.2-5) to 1.

Depending on their properties, the safeners can be used for pretreating the seed of the crop plant (seed dressing) or can be introduced into the seed furrows before sowing or can be used together with the herbicide before or after the emergence of the plants. Pre-emergence treatment includes both the treatment of the cultivated area before sowing and the treatment of cultivated areas which have been sown but are not yet covered with vegetation.

In principle, the safener can be used before, after or at the same time as the herbicide, but its simultaneous use in the form of tank mixtures or finished formulations is preferred.

The compositions may include or be applied together with additional herbicides as appropriate to the particular weed problem to be treated. In particular the compositions may be used in combination with a herbicide which is suitable for use in graminaceous crops.

The above described can be prepared as both dilute compositions, which are ready for immediate use, and concentrated compositions, which require to be diluted before use, usually with water. Preferably the compositions contain from 0.01% to 90% by weight of the active ingredient. Dilute compositions ready for use preferably contain from 0.01 to 2% of active ingredient, while concentrated compositions may contain from 20 to 90% of active ingredient, although from 20 to 70% is usually preferred.

The solid compositions may be in the form of granules, or dusting powders wherein the active ingredient is mixed with a finely divided solid diluent, e.g., kaolin, bentonite, kieselguhr, dolomite, calcium carbonate, talc, powdered magnesia, Fuller's earth and gypsum. They may also be in the form of dispersible powders or grains, comprising a wetting agent to facilitate the dispersion of the powder or grains in liquid. Solid compositions in the form of a powder may be applied as foliar dusts.

Liquid compositions may comprise a solution or dispersion of an active ingredient in water optionally containing a surface-active agent, or may comprise a solution or dispersion of an active ingredient in a water-immiscible organic solvent which is dispersed as droplets in water.

Surface-active agents may be of the cationic, anionic, or non-ionic type. The cationic agents are, for example, quaternary ammonium compounds (e.g. cetyltrimethylammonium bromide). Suitable anionic agents are soaps; salts or aliphatic mono esters of sulphuric acid, for example sodium lauryl sulphate; and salts of sulphonated aromatic compounds, for example sodium dodecylbenzenesulphonate, sodium, calcium, and ammonium lignosulphonate, butylnaphthalene sulphonate, and a mixture of the sodium salts of diisopropyl and triisopropylnaphthalenesulphonic acid. Suitable non-ionic agents are the condensation products of ethylene oxide with fatty alcohols such as oleyl alcohol and cetyl alcohol, or with alkylphenols such as octyl- or nonylphenol or octyl-cresol. Other non-ionic agents are the partial esters derived from long chain fatty acids and hexitol anhydrides, for example sorbitan monolaurate; the condensation products of the partial ester with ethylene oxide; and the lecithins.

The aqueous solutions or dispersions may be prepared by dissolving the active ingredient in water or an organic solvent optionally containing wetting or dispersing agent(s) and then, when organic solvents are used, adding the mixture so obtained to water optionally containing wetting or dispersing agent(s). Suitable organic solvents include, for example, ethylene di-chloride, isopropyl alcohol, propylene glycol, diacetone alcohol, toluene, kerosene, methylnaphthalene, the xylenes and trichloroethylene.

The compositions for use in the form of aqueous solutions or dispersions are generally supplied in the form of a concentrate containing a high proportion of the active ingredient, and the concentrate is then diluted with water before use. The concentrates are usually required to withstand storage for prolonged periods and after such storage, to be capable of dilution with water to form aqueous preparations which remain homogeneous for a sufficient time to enable them to be applied by conventional spray equipment. Concentrates conveniently contain 20–90%, preferably 20–70%, by weight of the active ingredient(s). Dilute preparations ready for use may contain varying amounts of the active ingredient(s) depending upon the intended purpose; amounts of 0.01% to 10.0% and preferably 0.1% to 2%, by weight of active ingredient(s) are normally used.

A preferred form of concentrated composition comprising the active ingredient which has been finely divided and which has been dispersed in water in the presence of a surface-active agent and a suspending agent. Suitable suspending agents are hydrophilic colloids and include, for example, polyvinylpyrrolidone and sodium carboxymethylcellulose, and the vegetable gums, for example gum acacia and gum tragacanth. Preferred suspending agents are those which impart thixotropic properties too, and increase the viscosity of the concentrate. Examples of preferred suspending agents include hydrated colloidal mineral silicates, such as montmorillonite, beidellite, nontronite, hectorite, saponite, and saucorite. Bentonite is especially preferred. Other suspending agents include cellulose derivatives and polyvinyl alcohol.

The rate of application of the compounds of the invention will depend on a number of factors including, for example, the compound chosen for use, the identity of the plants whose growth is to be inhibited, the formulations selected for use and whether the compound is to be applied for foliage or root uptake. As a general guide, however, an application rate of from 0.005 to 20 kilograms of cyclohexanedione herbicide per hectare is suitable while from 0.1 to 10 kilograms per hectare may be preferred.

The preparation of compounds of formula (I), (II), (III), (IV), (V) and (VI) are described in the respective patent applications.

The following preparations of some compounds of formula (III) are given by way of illustration.

PREPARATION 1

This preparation relates to the compound of formula:

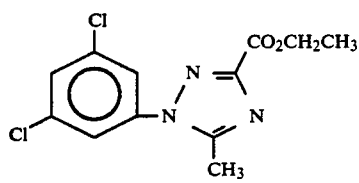

Step a

A suspension of diethylacetamidomalonate (67.34 g) in ethanol (100 ml) was prepared and a solution of potassium hydroxide (13.2 g) in ethanol (300 ml) added dropwise over three hours at room temperature. The mixture was stirred for 2 hours and left to stand overnight at room temperature. It was then cooled to 0° C. and acidified with concentrated hydrochloric acid (17.4 ml). The reaction mixture was then filtered to remove precipitated potassium chloride and the filtrate evaporated to dryness under reduced pressure. The product was recrystallised first from ethanol and then from ethylacetate to give the acetamidomalonate mono-ethylester in 61% yield.

Step b

Dichloroaniline (11.35 g) was almost completely dissolved in water (200 ml) and concentrated hydrochloric acid (20 ml) at 0° C., and a solution of sodium nitrite (5.34 g) in water (11.5 ml) was added dropwise. The solution was stirred for 10 minutes after addition and then filtered. The filtrate was added dropwise to a well stirred suspension of acetamidomalonate-monoethylester (13 g) in water (70 ml) at 6°–8° C. After addition the reaction mixture was brought to pH4–5 by the careful addition of solid sodium carbonate. A yellow precipitate formed along with $CO_2$ evolution. The reaction mixture was stirred for 1–1½ hours and the temperature allowed to rise to ca. 20° C. The precipitate was filtered off, washed with water and air dried.

The crude precipitate (still containing ca. 50 ml water) was recrystallised from ethanol (with the addition of charcoal before filtration) and dried to give yellow crystals (13.33 g) of the compound of formula:

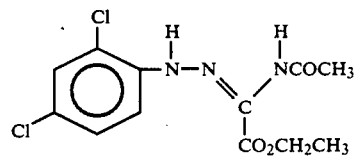

Step c

The ester amide from step (b) (10.9 g) was dissolved in acetic anhydride (150 ml) and heated under reflux for 2 hours. After this time, the solution was evaporated to dryness at 70° C. under reduced pressure to give a yellow oil which crystallised on cooling. Recrystallisation from methanol gave the desired compound as yellow crystals (9.02 g).

PREPARATION 2

This preparation illustrates the preparation of the compound of formula

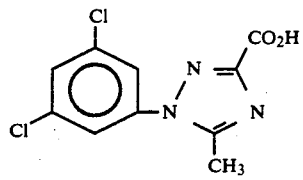

The ester from preparation 1 (2.5 g) was dissolved in warm isopropylalcohol (100 ml) and sodium hydroxide (0.35 g) in water (25 ml) added dropwise. A deep red solution was observed as the first drops of sodium hydroxide solution were added and then a paler precipitate came down during the subsequent addition. The reaction mixture was stirred for two hours, then evaporated to dryness under reduced pressure. The resultant product was dissolved in water (120 ml) and acidified with dilute hydrochloric acid to pH 1. The resulting precipitate was filtered, washed with water, and dried to give the desired compound (2.22 g).

The following Examples illustrate the invention.

EXAMPLE 1

The following formulations were prepared.

|  | % w/v |
|---|---|
| Formulation A | |
| 2-[1-(ethoxyimino)propyl]-3-hydroxy-5-(2,4,6 trimethylphenyl)cyclohex-2-en-1-one | 10 |
| Methyl capped nonyl phenol polyoxyethylene (N) (N = 30 oxyethlene units) | 2 |
| Sodium dioctylsulphosuccinate | 3 |
| Anisole | 40 |
| Solvesso 150 | to 100 |
| Formulation B | |
| 3,4-dichlorophenoxyacetonitrile | 10 |
| Methyl cyclohexanone | 90 to 100 |
| + Span 80 | 2.2 |
| + Tween 20 | 7.8 |

Formulation A was added to Formulation B at two fixed ratios's 2:1 and 1:1 in a tank-mix. A non-ionic surfactant 'Agral 90' was added to all treatment at a concentration of 0.1% in the final spray volume. The mixture was applied through a track sprayer to various species as shown in Table I at a volume of 200 l/ha.

TABLE I

| Species Composition of Test | | |
|---|---|---|
| Test Species | Leaf No. at treatment | Species Code |
| Winter wheat c.v Armada | 2 | Ww |
| Spring wheat c.v Timmo | 2–3 | Ws |
| Winter barley c.v Gerbel | 2–3 | By |
| Spring barley c.v Atem | 3 | Br |
| *Avena fatua* | 3 | Av |
| *Alopecurus myosuroides* | 2–3 | Al |
| *Lolium rigidum* | 3 | Lr |
| *Setaria viridis* | 3–5 | St |

All species were grown in compost in 3" pots.

The phytotoxicity was visually assessed at 7 DAT (crops only) and 25 DAT (weeds) on a 0–9 scale where 0=undistinguishable from control 9=dead.

<2 is the limit of acceptable phytotoxicity.
>7 is the level of effective weed control.

EXAMPLE 2

The following compounds were prepared as emulsifiable concentrates.

Herbicides

C  2-[1-(ethoxyimino)propyl]-3-hydroxy-5- (2,4,6-trimethylphenyl)cyclohex-2-en-1-one.

D  5-(3-butyryl-2,4,6-trimethylphenyl)-2-[1-ethoxyimino)-propyl]-3-hydroxycyclohex-2-en-1-one;

Additives

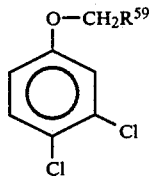

| No | $R^{59}$ |
|---|---|
| 1 | $-CSNH_2$ |
| 2 | $-COOH$ |
| 3 | $-COOCH_3$ |
| 4 | $-COOC_3H_7$ |
| 5 | $-CN$ |
| 6 | $-CONH_2$ |
| 7 | $-CO_2C_2H_5$ |

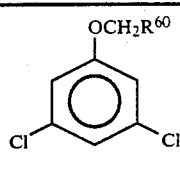

| No | $R^{60}$ |
|---|---|
| 8 | $CSNH_2$ |
| 9 | $-CON(CH_3)_2$ |
| 10 | $CO_2H$ |
| 11 | $CN$ |
| 12 | $CO_2C_2H_5$ |
| 13 | $CONH_2$ |
| 14 | $CO_2CH_3$ |
| 15 | $CO_2C_3H_7$ |

TABLE II

| | 7 DAT RESULTS *Summary of Crop Phytotoxicity 7 DAT | | | | | | | | | | | | | | | |
|---|---|---|---|---|---|---|---|---|---|---|---|---|---|---|---|---|
| | FORMULATION A | | | | | FORMULATION A + B AT 2:1 RATIO | | | | | | FORMULATION A + B AT 1:1 RATIO | | | | |
| | Rates g/ha | | | | | | | | | | | | | | | |
| A | 50 | 100 | 200 | 400 | 800 | A B | 50 25 | 100 50 | 200 100 | 400 200 | 800 400 | A B | 50 50 | 100 100 | 200 200 | 400 400 | 800 800 |
| Ww | 0 | 0 | 0 | 0.7 | — | | 0 | 0 | 0 | 0 | 0 | | — | — | — | — | — |
| Ws | 0.3 | 0 | 0 | 1.3 | — | | 0 | 0 | 0 | 0 | 0.3 | | — | — | — | — | — |
| By | 0.3 | 0 | 1.0 | 3.7 | — | | 0.3 | 0 | 0.3 | 0.3 | 0.7 | | — | — | — | — | — |
| Br | 0 | 0.3 | 0.7 | 4.0 | — | | 0 | 0 | 0 | 0 | 1.0 | | 0 | — | 0 | — | 1.0 |

*All results are the mean of 3 replicates, score meaned to 1 decimal place.

| | 25 DAT RESULTS *Summary of Weed Control 25 DAT | | | | | |
|---|---|---|---|---|---|---|
| | FORMULATION A | | FORMULATION A + B AT 2:1 RATIO | | FORMULATION A + B AT 1:1 RATIO | |
| | Rates g/ha | | | | | |
| A | 50 | 100 | A B | 50 25 | 100 50 | A B | 50 50 | 100 100 |
| Av | 8.0 | 8.0 | 8.0 | 8.3 | 8.0 | — |
| Al | 7.3 | 7.7 | 8.3 | 8.7 | — | — |
| Lr | 7.3 | 8.3 | 7.0 | 8.3 | — | — |
| St | 9.0 | 9.0 | 9.0 | 9.0 | — | — |

*Results are the mean of 3 replicates to 1 decimal place

-continued

Additives

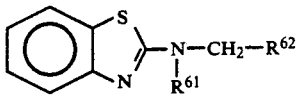

| No | R⁶¹ | R⁶² |
|---|---|---|
| 16 | H | COOC$_2$H$_5$ |

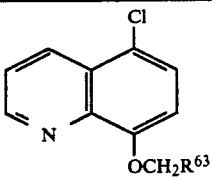

| No | R⁶³ |
|---|---|
| 17 | CONH$_2$ |
| 18 | CO$_2$H |
| 19 | CO$_2$CH$_3$ |

The above-mentioned concentrates were applied either alone or as tank-mixes in the glasshouse to the following species.

|  | Abbreviation |
|---|---|
| Winter Wheat | Ww |
| Spring Barley | Br |
| *Avena fatua* | Av |
| *Alopecurus myosuroides* | Al |
| *Lolium rigidum* | Lr |

All species were grown in 3 inch pots and were at approximately the two to three fully expanded leaves growth stage.

Formulations of herbicide C contained 0.1% Agral in the spray volume and formulations of herbicide D contained 1% Atplus were applied by foliar spray at a total volume of 200 l/ha.

Two assessments were made of the sprayed species, one at 7 days after treatment in order to assess the phytoxicity to the crop, and a second at 21 days after treatment to assess the activity against the weed species. The assessments were made on a scale of 0–9 where 0 is no effect and 9 is complete kill.

The results are shown in the following Table IV.

TABLE (IV)

| | | | | 1ST TEST | | | | |
|---|---|---|---|---|---|---|---|---|
| | Rate | | Rate | 7 DAT | | 21 DAT | | |
| Herbicide | g/ha | Additive | g/ha | Ww | Br | Av | Al | Lr |
| C | 400 | — | — | 1 | 5 | 9 | 9 | 8 |
| | 800 | — | — | 4 | 6 | 9 | 9 | 9 |
| C | 400 | 5 | 400 | 0 | 3 | 9 | 9 | 4 |
| | 800 | | 800 | 1 | 1 | 9 | 9 | 8 |
| C | 400 | 6 | 400 | 3 | 4 | 9 | 8 | 7 |
| | 800 | | 800 | 2 | 4 | 9 | 9 | 8 |
| C | 400 | 7 | 400 | 1 | 1 | 9 | 9 | 5 |
| | 800 | | 800 | 1 | 2 | 9 | 9 | 8 |
| C | 400 | 11 | 400 | 0 | 4 | 9 | 9 | 7 |
| | 800 | | 800 | 1 | 5 | 9 | 9 | 9 |
| C | 400 | 12 | 400 | 1 | 5 | 9 | 9 | 8 |
| | 800 | | 800 | 2 | 6 | 9 | 9 | 8 |
| C | 400 | 16 | 400 | 1 | 2 | 9 | 9 | 3 |
| | 800 | | 800 | 1 | 6 | 9 | 9 | 8 |
| D | 5 | — | — | 2 | 1 | 0 | 0 | 1 |
| | 20 | — | — | 6 | 7 | 4 | 6 | 9 |
| D | 5 | 11 | 100 | 2 | 1 | 3 | 0 | 1 |
| | 20 | | 100 | 1 | 5 | 5 | 8 | 5 |
| D | 5 | 13 | 100 | 2 | 2 | 1 | 0 | 0 |
| | 20 | | 100 | 2 | 6 | 3 | 5 | 3 |
| D | 5 | 12 | 100 | 1 | 1 | 0 | 0 | 1 |
| | 20 | | 100 | 1 | 2 | 5 | 7 | 4 |
| D | 5 | 16 | 100 | 1 | 1 | 0 | 0 | 1 |
| | 20 | | 100 | 3 | 6 | 6 | 6 | 2 |

| | | | | 2ND TEST | | | | |
|---|---|---|---|---|---|---|---|---|
| | Rate | | Rate | 7 DAT | | 21 DAT | | |
| Herbicide | g/ha | Additive | g/ha | Ww | Br | Av | Al | Lr |
| *C | 400 | — | — | 2 | 6 | 9 | 9 | 9 |
| | 800 | — | — | 6 | 6.7 | 9 | 9 | 9 |
| C | 400 | 1 | 400 | 1 | 6 | 9 | 9 | 9 |
| | 800 | | 800 | 3 | 6 | 9 | 9 | 9 |
| C | 400 | 2 | 400 | 1 | 5 | 9 | 9 | 9 |
| | 800 | | 800 | 3 | 3 | 9 | 9 | 9 |
| C | 400 | 3 | 400 | 1 | 3 | 9 | 9 | 7 |
| | 800 | | 800 | 2 | 2 | 9 | 9 | 9 |
| C | 400 | 4 | 400 | 2 | 1 | 9 | 9 | 9 |
| | 800 | | 800 | 1 | 3 | 9 | 9 | 7 |
| C | 400 | 8 | 400 | 1 | 5 | 9 | 9 | 9 |
| | 800 | | 800 | 2 | 3 | 9 | 9 | 9 |
| C | 400 | 9 | 400 | 2 | 6 | 9 | 9 | 9 |
| | 800 | | 800 | 3 | 7 | 9 | 9 | 9 |
| C | 400 | 10 | 400 | 2 | 5 | 9 | 9 | 9 |
| | 800 | | 800 | 2 | 6 | 9 | 9 | 9 |
| *D | 5 | — | — | 3.3 | 5.3 | 6.7 | 8 | 8 |
| | 20 | — | — | 5.3 | 7 | 9 | 9 | 9 |
| D | 5 | 2 | 100 | 2 | 2 | 6 | 2 | 3 |
| | 20 | | 100 | 7 | 6 | 9 | 9 | 9 |
| D | 5 | 10 | 100 | 2 | 3 | 0 | 0 | 1 |
| | 20 | | 100 | 3 | 6 | 9 | 8 | 9 |
| D | 5 | 14 | 100 | 1 | 2 | 0 | 0 | 3 |
| | 20 | | 100 | 2 | 5 | 6 | 9 | 8 |
| D | 5 | 15 | 100 | 2 | 2 | 8 | 4 | 6 |
| | 20 | | 100 | 7 | 7 | 9 | 9 | 9 |

| | | | | 3RD TEST | | | | |
|---|---|---|---|---|---|---|---|---|
| | Rate | | Rate | 7 DAT | | 21 DAT | | |
| Herbicide | g/ha | Additive | g/ha | Ww | Br | Av | Al | Lr |
| *C | 400 | — | — | 1.7 | 4.3 | 9 | 9 | 8.3 |
| | 800 | — | — | 2.3 | 6.3 | 9 | 9 | 9 |
| C | 400 | 17 | 400 | 0 | 0 | 9 | 9 | 6 |
| | 800 | | 800 | 0 | 0 | 9 | 9 | 9 |
| C | 400 | 18 | 400 | 0 | 0 | 9 | 9 | 6 |
| | 800 | | 800 | 0 | 0 | 9 | 9 | 9 |
| C | 400 | 19 | 400 | 0 | 1 | 9 | 8 | 7 |
| | 800 | | 800 | 1 | 1 | 9 | 9 | 6 |
| *D | 5 | — | — | 0.3 | 1.3 | 2 | 2.3 | 5.3 |
| | 20 | — | — | 6.7 | 7.7 | 9 | 9 | 9 |
| | 5 | 19 | 400 | 0 | 1 | 0 | 1 | 0 |
| | 20 | | 800 | 0 | 1 | 4 | 4 | 4 |

*Means of 3 replicates

EXAMPLE 3

The following test was carried out using herbicide D from Example 2. The herbicide was formulated into a 12.5% w/v emulsifiable concentrate formulation and a 6.25% w/v emulsifiable concentrate in a conventional manner.

The following additives were also formulated into either 10% w/v suspension concentrates or 10% w/v emulsifiable concentrates.

| Additive |
|---|

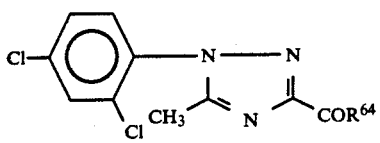

| No | $R^{64}$ |
|---|---|
| 20 | OH |
| 21 | $OC_2H_5$ |

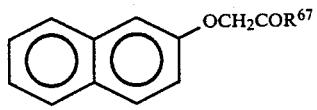

| No | $R^{65}$ | $R^{66}$ |
|---|---|---|
| 22 | $CH_3$ | $OCH_2CH_3$ |

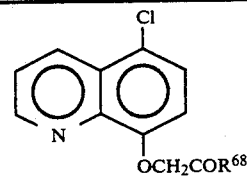

| No | $R^{67}$ |
|---|---|
| 23 | $OCH_2CH_3$ |

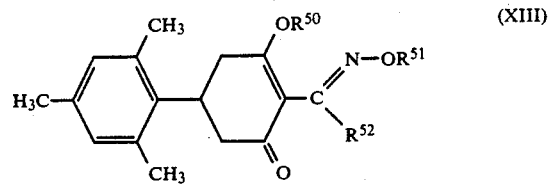

| No | $R^{68}$ |
|---|---|
| 24 | $OC_2H_5$ |
| 25 | $NH_2$ |

The herbicide formulation was tank-mixed with the various additive formulation in ratios of from 1:1 to 1:40 herbicide:additive. The mixtures were sprayed at 200 l/ha, the spray solution containing 0.1% Agral 90 onto the following test species.

| | Abbreviation |
|---|---|
| Maize cv Pioneer 3183 | Maize |
| *Digitaria sanguinalis* | DIGSA |
| *Echinochloa crus-galli* | ECHCG |
| *Setaria faberi* | SETFA |
| *Sorghum halepense* | SORHA |

Maize was grown in 5" pots and the grass weeds in 3" pots all in John Innes Potting Compost (JIP 3). Herbicide treatments were applied post-emergence with the maize having 3 to 5 leaves and the grasses 3 to 4 leaves. Each treatment consisted of maize and three or four grass weeds.

After treatment the plants were maintained in a glass house with watering, feeding and pest/disease control as required.

Plants were assessed for injury between 18 and 21 days after treatment. Injury was scored visually on a percentage scale where 0=no effect and 100=complete kill.

The results are shown in Table V.

TABLE V

| Herbicide Rate $gha^{-1}$ | Additive | Rate $gha^{-1}$ | Maize | DIGSA | ECHCG | SETFA |
|---|---|---|---|---|---|---|
| 1ST TEST % age plant injury 21 DAT | | | | | | |
| 9 | — | — | 95 | 98 | 100 | 100 |
|  | 20 | 100 | 5 | 100 | 100 | 100 |
|  | 21 | 100 | 20 | 100 | 100 | 95 |
|  | 24 | 100 | 0 | 100 | 100 | 100 |
| 18 | — | — | 100 | 100 | 100 | 100 |
|  | 25 | 100 | 0 | 100 | 100 | 100 |

| Herbicide Rate $gha^{-1}$ | Additive | Rate $gha^{-1}$ | Maize | DIGSA | ECHCG | SETFA | SORHA |
|---|---|---|---|---|---|---|---|
| 2ND TEST % age plant injury 18 DAT | | | | | | | |
| 18 | — | — | 83 | 100 | 100 | 95 | 87 |
|  | 23 | 100 | 5 | 100 | 100 | 100 | 100 |
|  | 22 | 100 | 0 | 100 | 100 | 100 | 100 |

When applied alone the herbicide caused unacceptable maize injury at rates required for adequate weed control. Addition of additives at an appropriate rate reduced the maize injury to an acceptable level while maintaining satisfactory weed control, addition of safener allowed selective use of the herbicide in the crop.

The additives alone had no effect on grasses up to 200 g ha$^{-1}$.

We claim:

1. A safened herbicidal composition comprising herbicidally effective amount of a compound selected from the group consisting of a compound of formula (XIII):

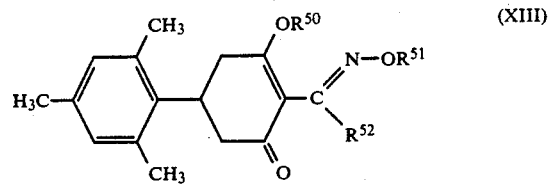

wherein:
$R^{50}$ is selected from hydrogen, sodium and potassium;
$R^{51}$ is ethyl;
$R^{52}$ is selected from ethyl and n-propyl; and a compound of formula (XIV):

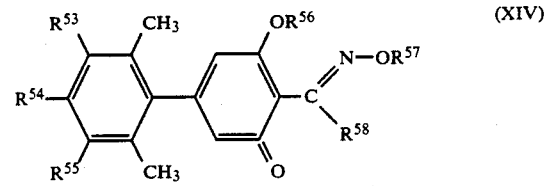

wherein:

$R^{53}$ is selected from the group consisting of methylmercapto, nitromethyl, methoxymethyl, ethoxymethyl, methylsulfinyl, methylsulfonyl, acetyl, propionyl, butyryl, sulfamoyl and N,N-di(methyl)sulfamoyl;

$R^{54}$ is selected from hydrogen and methyl;

$R^{55}$ is selected from hydrogen, methyl and ethyl;

$R^{56}$ is selected from hydrogen, sodium and potassium;

$R^{57}$ is ethyl;

$R^{58}$ is selected from ethyl and n-propyl; and a safening amount of a compound selected from the group consisting of a compound of formula (VII) or (IX):

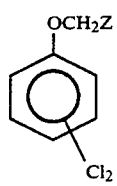 (VII)

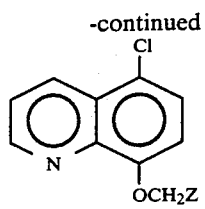 (IX)

where Z is —CSNH$_2$, —COOH, —COOCH$_3$, —COOC$_3$H$_7$, —CN, —CONH$_2$, CO$_2$C$_2$H$_5$ or —CON(CH$_3$)$_2$ in the case of the compound of formula VII and Z is —CONH$_2$, —COOH or CO$_2$CH$_3$ in the case of the compound of formula IX provided that when the compound is of formula VII and Z is —COOH, the two Cl substituents are in the 3,4-positions.

2. A composition according to claim 1 wherein the herbicidal compound is a compound of formula (XIII) and the safening compound is one having the formula (VII) wherein Z is —CN.

3. A composition according to claim 2 wherein the two compounds are present in a ratio of 1:1 by weight.

4. A process for killing or controlling weeds in crop plants which process comprises applying to the weeds and crops or to the locus thereof an effective amount of the composition of claim 1.

* * * * *